(12) United States Patent
Eggert et al.

(10) Patent No.: US 10,549,034 B2
(45) Date of Patent: Feb. 4, 2020

(54) ACTUATION STEP FAILURE HANDLING

(71) Applicant: Sanofi-Aventis Deutschland GMBH, Frankfurt am Main (DE)

(72) Inventors: Ilona Eggert, Frankfurt am Main (DE); Michael Caspers, Frankfurt am Main (DE); Muriel Didier, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 91 days.

(21) Appl. No.: 14/916,816

(22) PCT Filed: Sep. 8, 2014

(86) PCT No.: PCT/EP2014/069065
§ 371 (c)(1),
(2) Date: Mar. 4, 2016

(87) PCT Pub. No.: WO2015/036359
PCT Pub. Date: Mar. 19, 2015

(65) Prior Publication Data
US 2016/0213842 A1     Jul. 28, 2016

(30) Foreign Application Priority Data

Sep. 10, 2013   (EP) .................................. 13183728

(51) Int. Cl.
*A61M 5/14* (2006.01)
*A61M 5/172* (2006.01)
*A61M 5/142* (2006.01)

(52) U.S. Cl.
CPC ............ *A61M 5/172* (2013.01); *A61M 5/142* (2013.01); *A61M 2005/1402* (2013.01); *A61M 2205/702* (2013.01)

(58) Field of Classification Search
CPC ...... A61M 5/172; A61M 5/142; A61M 5/145; A61M 5/1452; A61M 5/16831;
(Continued)

(56) References Cited

U.S. PATENT DOCUMENTS

2007/0191770 A1   8/2007   Moberg et al.
2012/0116311 A1*  5/2012   Bruggemann .... A61M 5/14244
                                                604/154

FOREIGN PATENT DOCUMENTS

CA    2779553 A1 *  6/2011   .............. A61M 5/19
CA    2779553 A1 *  6/2011   ........ A61M 5/14244
(Continued)

OTHER PUBLICATIONS

International Search Report and Written Opinion in International Application No. PCT/EP2014/069065, dated Oct. 1, 2014, 11 pages.
(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

An apparatus for automatic ejection of a fluid includes a drive train for automatically ejecting the fluid from a fluid reservoir through an ejection channel, and a control unit for controlling the apparatus. The control unit is configured to detect failures of drive train actuation steps, during which the drive train is actuated for priming or fluid dose ejection. The control unit is further configured to control the apparatus as a function of an actuation step failure number. The actuation step failure number is the number of failed drive train actuation steps since the last successful drive train actuation step.

20 Claims, 11 Drawing Sheets

(58) Field of Classification Search
CPC ............ A61M 5/20; A61M 2005/1402; A61M 2205/273; A61M 2205/276; A61M 2205/52; A61M 2205/702
See application file for complete search history.

(56) References Cited

FOREIGN PATENT DOCUMENTS

| | | | | |
|---|---|---|---|---|
| JP | 2012-513786 | 6/2012 | | |
| JP | 2013-512060 | 4/2013 | | |
| WO | WO 1996/027398 | 9/1996 | | |
| WO | WO 1997/033638 | 9/1997 | | |
| WO | WO 2007/015836 | 2/2007 | | |
| WO | WO 2010/076275 | 7/2010 | | |
| WO | WO 2011/067187 | 6/2011 | | |
| WO | WO-2012072556 A1 * | 6/2012 | .............. | A61M 5/19 |

OTHER PUBLICATIONS

International Preliminary Report on Patentability in International Application No. PCT/EP2014/069065, dated Mar. 15, 2016, 7 pages.

Rote Liste, "50. Hypophysen-, Hypothalamushormone, andere regulatorische Peptide u. ihre Hemmstoffe," Chapter 50, ed. 2008, 20 pages.

* cited by examiner

ACTUATION STEP FAILURE HANDLING

CROSS-REFERENCE TO RELATED APPLICATIONS

This application is a U.S. national stage application under 35 USC § 371 of International Application No. PCT/EP2014/069065, filed on Sep. 8, 2014, which claims priority to European Patent Application No. 13183728.8, filed on Sep. 10, 2013, the entire contents of which are incorporated herein by reference.

TECHNICAL FIELD

The present patent application inter-alia relates to an apparatus for automatic ejection of a fluid having a drive train for automatically ejecting the fluid from a fluid reservoir through an ejection channel.

BACKGROUND

A medical device can be an injector, for example a hand-held injector, especially a pen-type injector, that is an injector of the kind that provides for administration by injection of medicinal products from one or more multidose cartridges. Certain aspects of the present invention relate to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

There is a general desire to improve handling and user safety of medical devices, in particular in the event of an operational failure. Such an operational failure may for example be an ejection channel blocking event, in which the ejection channel for ejecting a medicament is blocked, for example by a blocked needle forming part of the ejection channel. A blocked needle can have different causes like for example fibrillation of the medicament liquid, a destroyed or deformed needle tip, for example due to needle reuse, or improper manufacturing. For example, during injection of a medicament such as insulin with a medical device, it may happen that a needle such as the injection needle is blocked so that the medicament cannot be ejected at the regular rate or even at all, which brings about a risk of medicament underdosing. To improve handling and user safety of a medical device or similar apparatuses, it is therefore desirable to adequately handle such blocked needle failures.

For a medical device, in which medicament injection is mechanically actuated by the user, like in a mechanical pen, the blocked needle is likely to be recognized by the user because of an increased injection force through the mechanical dose button. However, with an electro-mechanical device the injection is automatically performed by the device so that the user does not necessarily recognize the device's malfunction.

Handling a situation, in which a medicament cannot be injected from the medical device at regular rate or at all, is however problematic as there may be different causes for such a failure. In particular, the blocking may be caused by different components of the medical device or components attached thereto. A similar ejection failure may however arise if the drive train of the device is defective.

In light of the aforementioned, certain aspects of the invention face the technical problem of providing an apparatus, in particular a medical device, for automatic ejection of a fluid with an improved failure handling, so that a user is able to recognize and remedy typical malfunctions while at the same time user safety is maintained.

Certain aspects of the present invention provide a corresponding system comprising such an apparatus and a method for controlling such an apparatus.

In some aspects, an apparatus for automatic injection of a fluid has a drive train for automatically injecting the fluid from a fluid reservoir through an ejection channel and a control unit for controlling the apparatus, the control unit being configured to detect failures of drive train actuation steps, during which the drive train is actuated for priming or fluid dose ejection, the control unit being further configured to control the apparatus as a function of an actuation step failure number, the actuation step failure number being the number of failed drive train actuation steps since the last successful drive train actuation step.

The apparatus may be a delivery device, especially a drug delivery device such as a medical device configured to eject a drug agent (e.g. a dose of a medicament) such as an infusion device or an injection device, for instance and insulin injection pen. Injection devices may be used either by medical personnel or by patients themselves. As an example, type-1 and type-2 diabetes may be treated by patients themselves by injection of insulin doses, for example once or several times per day.

In particular, the apparatus may be a medical device configured to deliver (e.g. eject) at least two drug agents from separate cartridges situated in two separate retainers.

Alternatively the apparatus may for instance be configured to deliver (e.g. eject) a two-component adhesive from separate cartridges comprising a first component of the two-component adhesive (e.g. a binder) and a second component of the two-component adhesive (e.g. a hardener), respectively.

The apparatus is an apparatus for automatic ejection of a fluid. "Automatic" in this sense is understood to mean that the actual ejection of a fluid is not directly performed by a user, for example by pressing a piston of a syringe to eject the fluid, but is performed by the apparatus itself employing an electrically driven drive train, for example after a user has initiated the ejection by pressing an ejection button of the device.

The apparatus comprises a drive train for automatically ejecting the fluid from the fluid reservoir through an ejection channel. The fluid reservoir may be accommodated in the apparatus. For example, the apparatus may comprise one or more retainers to accommodate one or more cartridges each containing a fluid to be ejected from the apparatus. The ejection channel is a channel to provide fluid communication during automatic ejection of the fluid between the fluid reservoir and the place where the fluid is to be ejected to, in particular an outlet of the apparatus or of a component attached to the apparatus such as a dispense interface or a needle assembly. The ejection channel may also comprise elements for controlling the fluid flow through the ejection channel, such as valves for example.

The apparatus has a control unit for controlling the apparatus. The control unit is preferably a micro-processor control unit comprising a micro-processor and a storage such as a RAM, a ROM, a flash memory, a hard disk or the like containing commands the execution of which by the micro-processor causes controlling of the apparatus, in particular actuation of the drive train. The control unit is configured to detect failures of drive train actuation steps, during which the drive train is actuated for priming or fluid dose ejection.

A drive train actuation step, during which the drive train is actuated for priming, (drive train actuation step for priming) is understood to mean a step, during which the drive train is actuated such that a certain amount of fluid is expelled from the fluid reservoir to fill the volume of the ejection channel and/or to check whether the fluid channel is blocked or not.

For example, if a disposable assembly attached to the apparatus and forming part of the ejection channel is replaced, the void ejection channel part of the replaced disposable assembly is to be filled with the fluid. By performing such a drive train actuation step for priming, for example after replacement of a disposable assembly, the dosing accuracy of the apparatus is improved, since the ejection channel does not contain air or the like when initiating fluid dose ejection. A drive train actuation step for priming is particularly important for medical devices such as medicament delivery devices, since in this way air is removed from the ejection channel, which otherwise could cause severe complications such as air embolisms. Furthermore, a drive train actuation step for priming may also be used to check whether the apparatus is functioning properly, for example by checking that it is not blocked, before performing a drive train actuation step for fluid dose injection.

A drive train actuation step, during which the drive train is actuated for a fluid dose ejection, (drive train actuation step for fluid dose ejection) is understood to mean a step, during which the drive train is actuated such that a defined dose of a fluid is expelled from the fluid reservoir to be ejected out of the apparatus. To this end, the drive train may be advanced towards the fluid reservoir, so that fluid from the fluid reservoir is ejected through the ejection channel and out of the apparatus. If the apparatus is for example a medicament delivery device, the drive train actuation step for fluid dose ejection may comprise ejection of a specific medicament dose from the delivery device to a patient.

The control unit is configured to detect failures of at least one or both of the drive train actuation steps for fluid dose ejection and the drive train actuation steps for priming. Since both drive train actuation steps comprise actuation of the drive train, the control unit may in particular be configured to detect failures of the drive train movement, such as for example stalling of the drive train.

The control unit is further configured to control the apparatus as a function of an actuation step failure number. The actuation step failure number is the number of failed drive train actuation steps since the last successful drive train actuation step. This is understood to mean that the actuation step failure number is the number of successive drive train actuation steps for which the control unit has detected a failure.

For example, after a first failed drive train actuation step the actuation step failure number equals 1. After two consecutive failed drive train actuation steps, the actuation step failure number equals 2. After four drive train actuation steps, of which only the second one was successful, the actuation step failure number equals 2 as it is only counted from the last successful drive train actuation step.

Controlling the apparatus as a function of an actuation step failure number is understood to mean that the control unit selects and/or controls at least one step of the apparatus to be performed as a function of the actuation step failure number.

Controlling an apparatus as a function of the actuation step failure number provides an advanced failure handling, which improves the usability of the apparatus while at the same time maintaining user safety. It was found that similar failures during drive train actuation steps may be caused by different types of malfunctions of the apparatus. The apparatus described above in particular allows sequential handling of different failure sources for a failure persisting over several drive train actuation steps.

In some aspects, a system includes an apparatus as described above and a disposable assembly attachable to the apparatus.

In some aspects, a method for controlling an apparatus, in particular an apparatus as the apparatus described above, the apparatus having a drive train for automatically ejecting a fluid from a fluid reservoir through an ejection channel, includes the following steps: detecting of failures of drive train actuation steps, during which the drive train is actuated for priming or fluid dose ejection; and controlling of the apparatus as a function of an actuation step failure number, the actuation step failure number being the number of failed drive train actuation steps since the last successful drive train actuation step.

A number of embodiments of the apparatus, the system and the method will be described in the following. Although these embodiments are described in particular with reference to the apparatus, they are not limited to the apparatus, but also apply to the system comprising such an apparatus and to the method for controlling an apparatus such as the apparatus described above, accordingly.

According to an embodiment of the apparatus the control unit is configures to detect a failure of a drive train actuation step by detecting stalling of the drive train during the drive train actuation step. It was found that several prevalent failure sources of the apparatus such as a blocked needle or a blocked fluid path or a drive train malfunction cause stalling of the drive train. Detection of drive train stalling therefore is a reliable way for detecting the occurrence of a number of different failures. For stalling detection the stall sensor may for example be configured to monitor the voltage/current profile of the drive train actuator or to optically monitor the movement of a motor of the drive train by means of an optical encoder containing an optical sensor. To this end, the optical sensor may for example be triggered by one or more flags mounted on the axis of the motor of the drive train. When during rotation of the motor the one or more flags rotate around the motor axis, light is alternately directed to or blocked from the optical sensor. The optical sensor generates an electronic signal that represents the number of rotations of the motor around the motor axis. The stall sensor may then detect stalling of the drive train by detecting missing steps of the drive train movement from this electronic signal. An exemplary implementation for such a stall sensor is described in WO 2010/076275 A1.

According to a further embodiment the apparatus comprises a housing with a connector for removably attaching thereto a disposable assembly, the disposable assembly forming part of the ejection channel when attached to the connector, wherein the control unit is configured to cause a replacement step for the disposable assembly or a part thereof after detection of a failure of a drive train actuation step if the actuation step failure number is within a predetermined replacement number range.

The disposable assembly may for example be a dispense interface, in particular a dispense interface with a needle hub connector, so that a disposable needle or a needle assembly can be attached thereto. The disposable assembly may also be a needle assembly to be directly attached to the connector of the housing. Further, the disposable assembly may also be a dispense interface with a needle assembly attached thereto. In this case, the dispense interface may be regarded as a first part and the needle assembly may be regarded as a second part of the disposable assembly or vice versa. The disposable assembly forming part of the ejection channel may be a cause for a failure during a drive train actuation step. For example, if the disposable assembly is a dispense interface, a needle of the dispense interface or a disposable needle attached thereto may be blocked. Blocking of a needle may occur more often than blocking of another part of the ejection channel as the needles usually have a relatively small cross section. Moreover, disposable assemblies are often designed for a shorter life-time than the apparatus, so that disposable assemblies may also be more prone to failures. As failures of disposable assemblies may however be easily handled by the user by replacing the disposable assembly or part of it, the embodiment described above allows the user to handle these typical causes of failures.

The predetermined replacement number range defines the actuation step failure numbers for which the replacement step for the disposable assembly is to be performed. Since replacement of a disposable assembly or a part thereof may be easily handled by the user, the predetermined replacement number range preferably covers the range of from 1 to N, wherein N equals 1, 2, 3 or a higher natural number. For example, if the predetermined replacement number range equals the range of from 1 to 2, the replacement step for the disposable assembly or part thereof is performed when the actuation step failure number equals 1 or 2, i.e. on the first two occurrences of a drive train actuation step failure.

A replacement step for the disposable assembly or a part thereof is understood to mean a step in which the control unit asks and/or forces the user to replace the disposable assembly or part thereof.

The embodiment described above may also cover the situation that the user has forgotten to attach the disposable assembly (such as a dispense interface or a needle assembly) to the apparatus. For example, the disposable assembly may provide the ejection channel, e.g. by a needle of a dispense interface puncturing a membrane of a fluid containing cartridge and thereby providing fluid communication between the cartridge and an outlet of the dispense interface or a needle assembly attached thereto. If the user has forgotten to attach such a disposable assembly to the apparatus, the ejection channel may then be blocked by the membrane of the cartridge, so that the drive train stalls when actuated as pressure builds up within the cartridge. In such a case, the replacement step has actually the function of an attachment step as the user is reminded that he forgot to attach the disposable assembly (such as the needle assembly and/or the dispense interface).

According to a further embodiment the apparatus further comprises a user interface for outputting messages to the user and the replacement step comprises outputting of a replacement message by means of the user interface. The user interface may for example be a graphical display such as an LCD/TFT display, a group of light emitting diodes, an illuminatable button such as an illuminatable dose button, a speaker for emitting a sound, a vibration alarm or the like. Outputting a message may accordingly comprise displaying a text or a symbol on a graphical display, displaying a light pattern by means of light emitting diodes, illuminating a button such as causing a button like the dose button to blink, outputting a sound by means of the speaker and/or turning on the vibration alarm or the like. By outputting a replacement message, the user may be informed that a problem has occurred and asked to replace the disposable assembly or a part thereof in an attempt to remedy the problem.

According to a further embodiment of the apparatus the replacement step comprises setting the apparatus into a status, in which a further drive train actuation step for priming or fluid dose ejection is only allowed after detection of a replacement of the disposable assembly or part thereof. To this end, the apparatus may in particular comprise a sensor for detecting attaching/detaching of the disposable assembly in order to detect whether the disposable assembly has been replaced. This embodiment increases usability and user safety of the apparatus as the control unit ensures that the user does not ignore the replacement step.

Detection of a replacement of the disposable assembly or part thereof may in particular comprise detection of the disposable assembly or part thereof being detached from the apparatus and a disposable assembly or part thereof being attached to the apparatus.

Detection of a replacement of the disposable assembly or part thereof may or may not comprise detection whether the disposable assembly or part thereof attached to the apparatus is new or at least different from the disposable assembly or part thereof detached before. While detection whether the disposable assembly or part thereof is new or different increases user safety, this detection may be dispensed with for an easier and/or cheaper implementation.

The control unit may set the apparatus into a status, in which a drive train actuation for priming or fluid dose ejection is disallowed until a replacement of the disposable assembly or part thereof has been performed and/or detected. Setting the apparatus into a particular status may for example comprise setting a status variable in a storage of the control unit to a predefined value, wherein the control unit is configured such that at least one of the possible further control steps of the apparatus is a function of the status variable. For example, value "0" in the status variable may indicate regular operation, "1" may indicate a stand-by status and "2" may indicate a status, in which actuation of the drive train is disallowed. Alternatively, setting the apparatus into a particular status may for example comprise jumping to a particular position in the program flow of a computer program run by the control unit, such as a particular subroutine or a particular command sequence.

According to a further embodiment of the apparatus the replacement step comprises setting the apparatus into a status, in which a further drive train actuation step fluid dose ejection is only allowed after a successful drive train actuation step for priming. Performing a failure handling step like for example replacing a disposable assembly does not guarantee that the failure has been completely removed since the failure may have another or a different cause or since for example the replaced component may be defective as well. Therefore, there may still be a risk of improper fluid dose ejection, for example of an underdosing. According to the embodiment described above, this requires performance of a successful drive train actuation step for priming before allowing further drive train actuation steps for fluid dose ejection. Thus, this ensures that the apparatus functions properly before ejecting further fluid doses.

According to a further embodiment of the apparatus the control unit is configured to cause a replacement step for a first part of the disposable assembly after detection of a failure of a drive train actuation step if the actuation step failure number is within a predetermined first part replacement number range, and the control unit is further configured to cause a replacement step for a second part of the disposable component after detection of a failure of a drive train actuation step if the actuation step failure number is within a predetermined second part replacement number range, wherein the first part replacement number range differs from the second part replacement number range.

Disposable assemblies may consist of different parts, which individually may cause a failure of the apparatus. For example, a disposable assembly may comprise a disposable dispense interface and a disposable needle assembly configured to be attached to the dispense interface. In this case, the dispense interface may be regarded as a first part and the needle assembly may be regarded as a second part of the disposable assembly or vice versa. The embodiment described above allows handling failures of a drive train actuation step by dealing with the individual parts of the disposable assembly as potential failure sources. For example, if for this embodiment the first part is identified with a needle assembly and the second part is identified with the dispense interface, a replacement step for the needle assembly may be performed if the actuation step failure number equals 1 or 2 and, if the failure is not removed by then, a replacement step for the more expensive dispense interface may be performed if the actuation step failure number equals 3. In this way replacement steps may first be performed for parts that are cheaper or easier to replace, which improves cost-effectiveness and usability of the apparatus.

The first part replacement number range differs from the second part replacement number range. This is understood to mean that the first part replacement number range comprises a number that is not in the second part replacement number range and/or that the second part replacement number range comprises a number that is not in the first part replacement number range.

According to a further embodiment of the apparatus the control unit is configured to cause a system failure step if the actuation failure number is equal or greater than a predetermined system failure threshold number. The system failure step preferably comprises setting the apparatus into a status, in which further drive train actuation steps for fluid dose ejection and, optionally, priming are permanently disallowed. A failure of a drive train actuation step may be caused by a malfunction that can be handled easily by the user, for example by replacing a disposable assembly or part thereof. However such failures may also be caused by failures that are difficult to handle or are severe so that the proper functioning of the apparatus cannot be guaranteed. In the latter case, the apparatus has to be analyzed and repaired by skilled service personnel or even to be replaced by a new apparatus. The embodiment described above ensures that after a defined number of consecutive failed drive train actuation steps the apparatus can no longer be used for fluid dose ejection. This improves user safety since the user is prevented from using faulty apparatuses.

The predetermined system failure threshold number may equal 1 so that for complex or critical apparatuses a fluid dose ejection is disallowed once a failure of a drive train actuation step has occurred. However, the predetermined system failure threshold number preferably equals to a number larger than 1, so that the user has a number of attempts to remedy the failure. For example, the predetermined system failure threshold number may equal 4, so that the user has three attempts to remedy the failure for example by replacing components of the apparatus such as a disposable assembly or parts thereof before the apparatus disallows further drive train actuation steps.

According to a further embodiment of the apparatus the control unit is configured to cause the following as a function of the ejection failure number after detection of a failure of a drive train actuation step:

a first part replacement step if the ejection failure number is within a predetermined first part replacement number range, the first part replacement step comprising: outputting of a first part replacement message to the user by means of a user interface of the apparatus and, optionally, setting the apparatus into a status, in which a further drive train actuation step is only allowed after detection of a replacement of a first part of a disposable assembly, and setting the apparatus into a status in which a further drive train actuation step for fluid dose ejection is only allowed after a successful drive train actuation step for priming;

a second part replacement step if the ejection failure number is within a predetermined second part replacement number range, the second part replacement step comprising: outputting of a second part replacement message to the user by means of the user interface and, optionally, setting the apparatus into a status in which a further drive train actuation step is only allowed after detection of a replacement of a second part of the disposable component, and setting the apparatus into a status in which a further drive train actuation step for fluid dose ejection is only allowed after a successful drive train actuation step for priming; and a system failure step if the actuation failure number is equal or greater than a predetermined system failure threshold number, the system failure step comprising: setting the apparatus into a status in which further drive train actuation steps for fluid dose ejection and, optionally, for priming are permanently disallowed.

For example, the disposable assembly may be a dispense interface with a needle assembly attachable thereto, wherein the needle assembly forms the first part and the dispense interface forms the second part of the disposable assembly. The first part replacement number range may be the range of 1 to 2, the second part number range may equal the number 3 and the predetermined system failure threshold number may equal the number 4.

It was found that the embodiment just described allows sequential handling of different failure sources of drive train actuation steps so that there is an increased likelihood to remedy the failure. At the same time safe operation of the apparatus is guaranteed since the apparatus does not allow further drive train actuation steps for fluid dose ejection after a number of attempts to remedy the failure, in particular after the failure sources that can be handled by the user have been tested without result.

According to a further embodiment the apparatus comprises a button to initiate a fluid dose ejection step. With this button a user may initiate a fluid dose ejection step. The execution of the fluid dose ejection step is controlled by the control unit which therefore still may allow or disallow the actual execution of the fluid ejection, i.e. the corresponding actuation of the drive train, depending on the status of the apparatus. The control unit may in particular cause deactivation of the button may if the apparatus is in a status in which further drive train actuation steps for fluid dose ejection and, optionally, priming are permanently disallowed.

According to a further embodiment the apparatus is a medical device, in particular a medicament injection device. Operational safety is in particular important for medical devices, in particular for medicament injection devices. With the apparatus described above, the risk of underdosing or unpredictable operation of a medical device may be reduced so that user safety is increased.

According to a further embodiment of the apparatus the apparatus is hand-held. Hand-held apparatuses are often apparatuses that are operated by laymen such as patients instead of particularly skilled personnel. The safety and usability increase achieved with the apparatus described above is therefore in particular advantageous for hand-held apparatuses.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
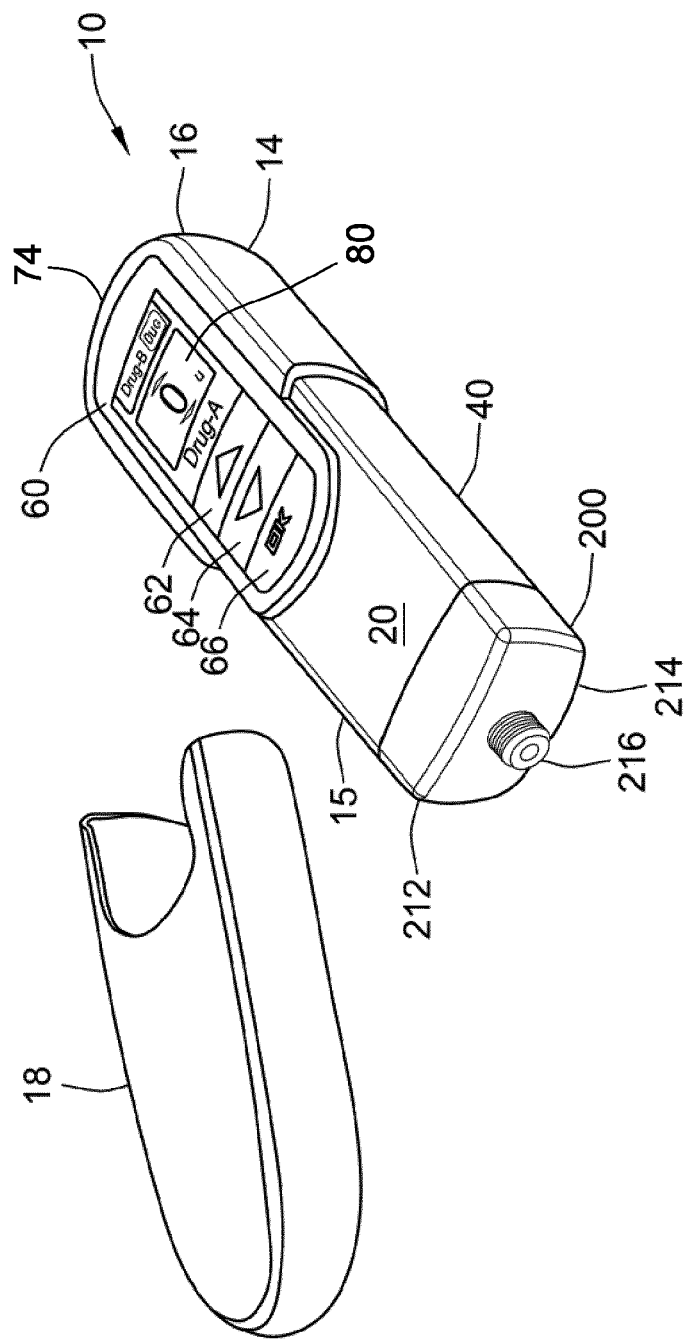
FIG. 1 illustrates a perspective view of a delivery device with an end cap of the device removed.
Figure 2:
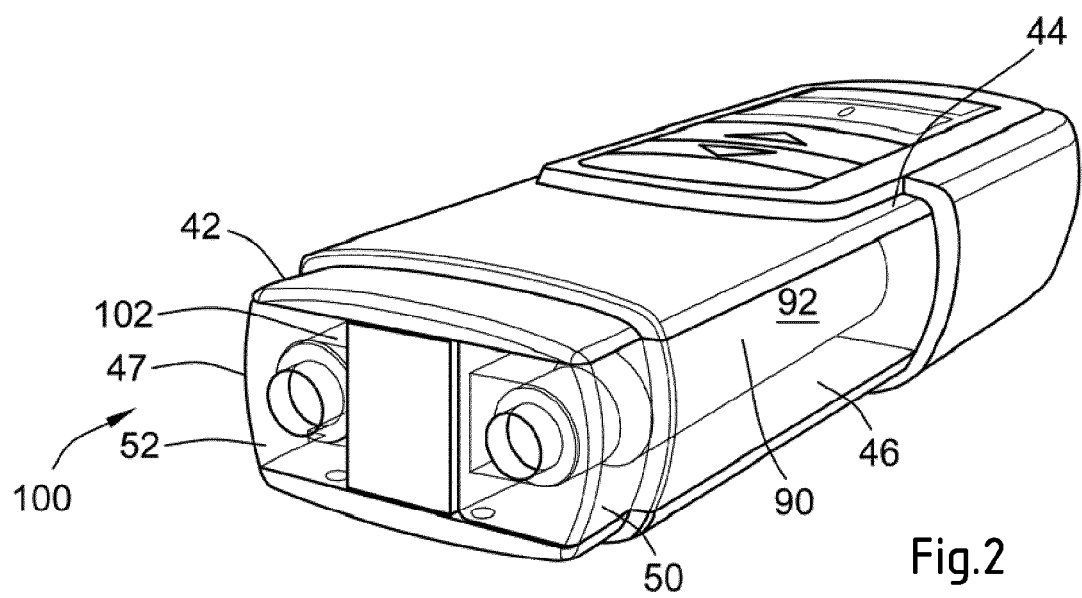
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament.

When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
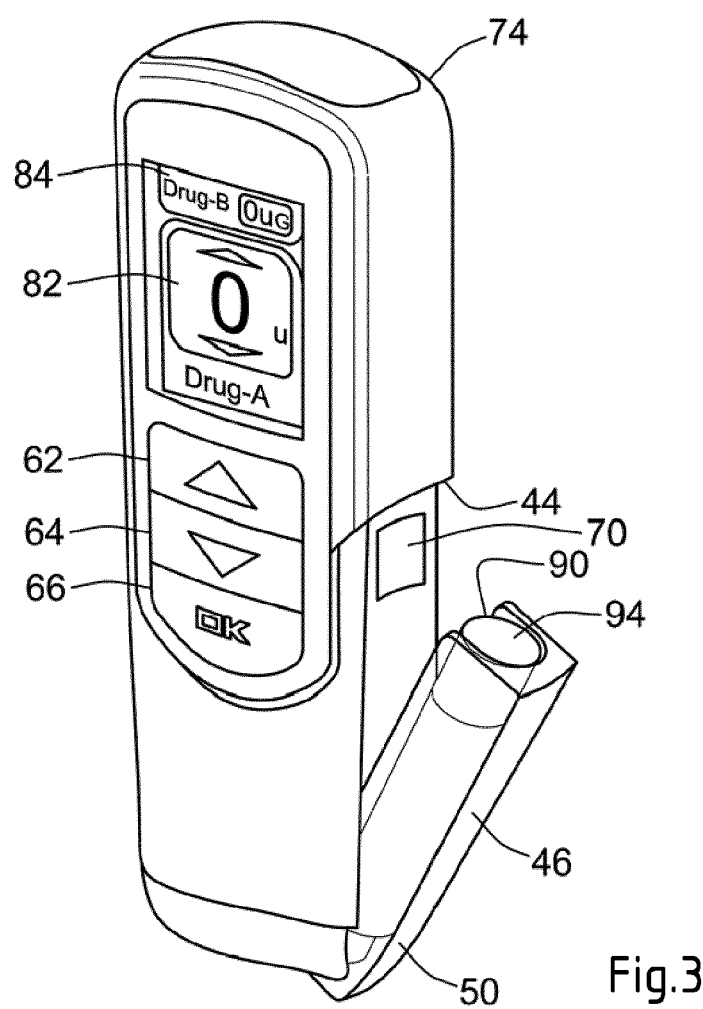
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
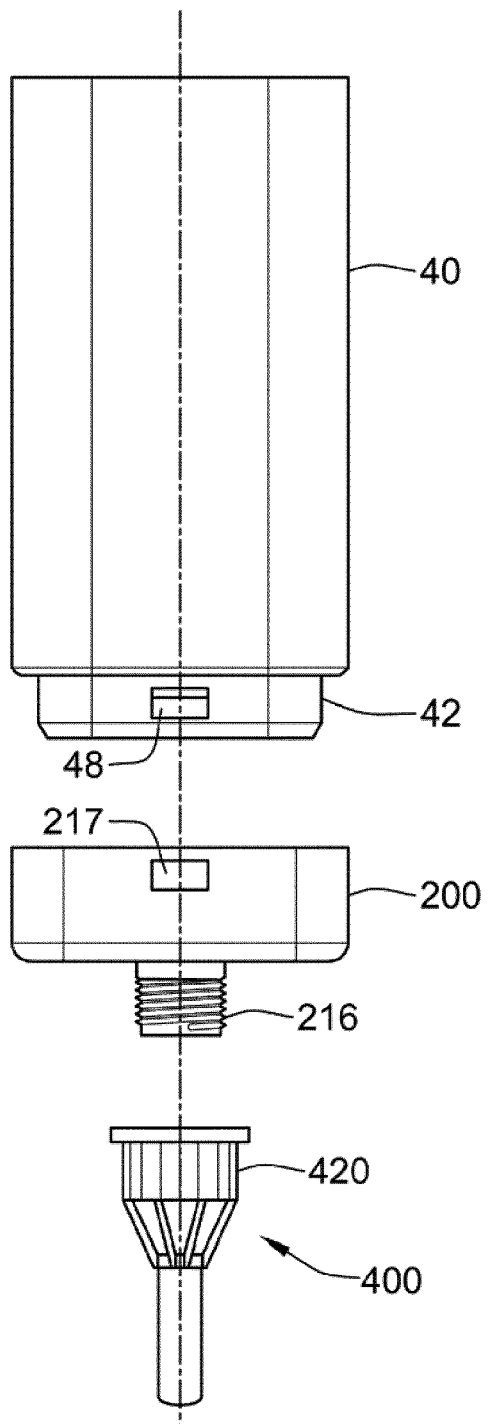
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
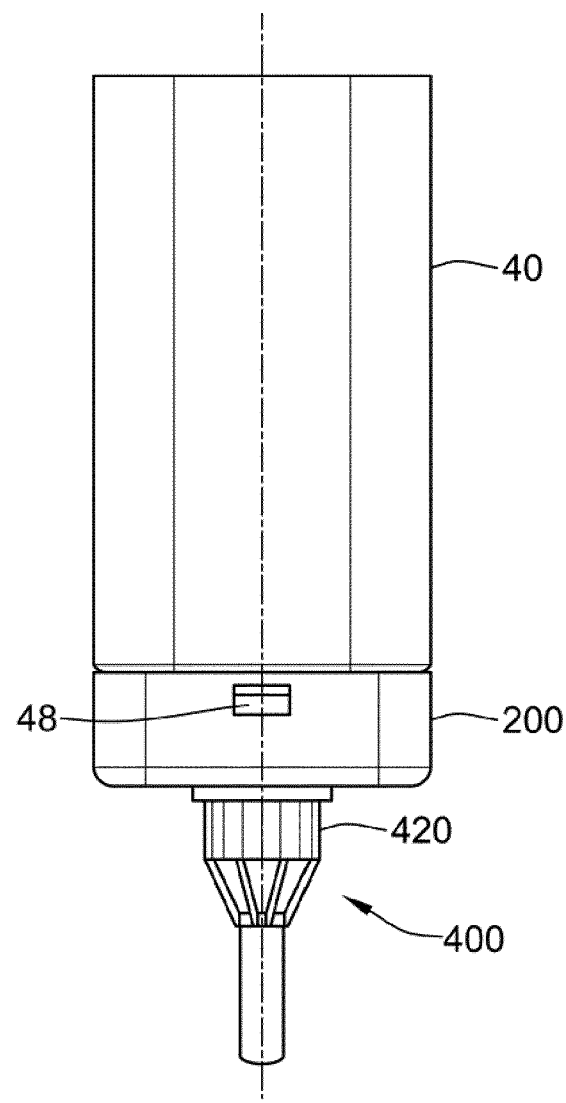
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. A connector 48 on the dispense interface 200 allows connection between the dispense interface 200 and the cartridge holder 40 and can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
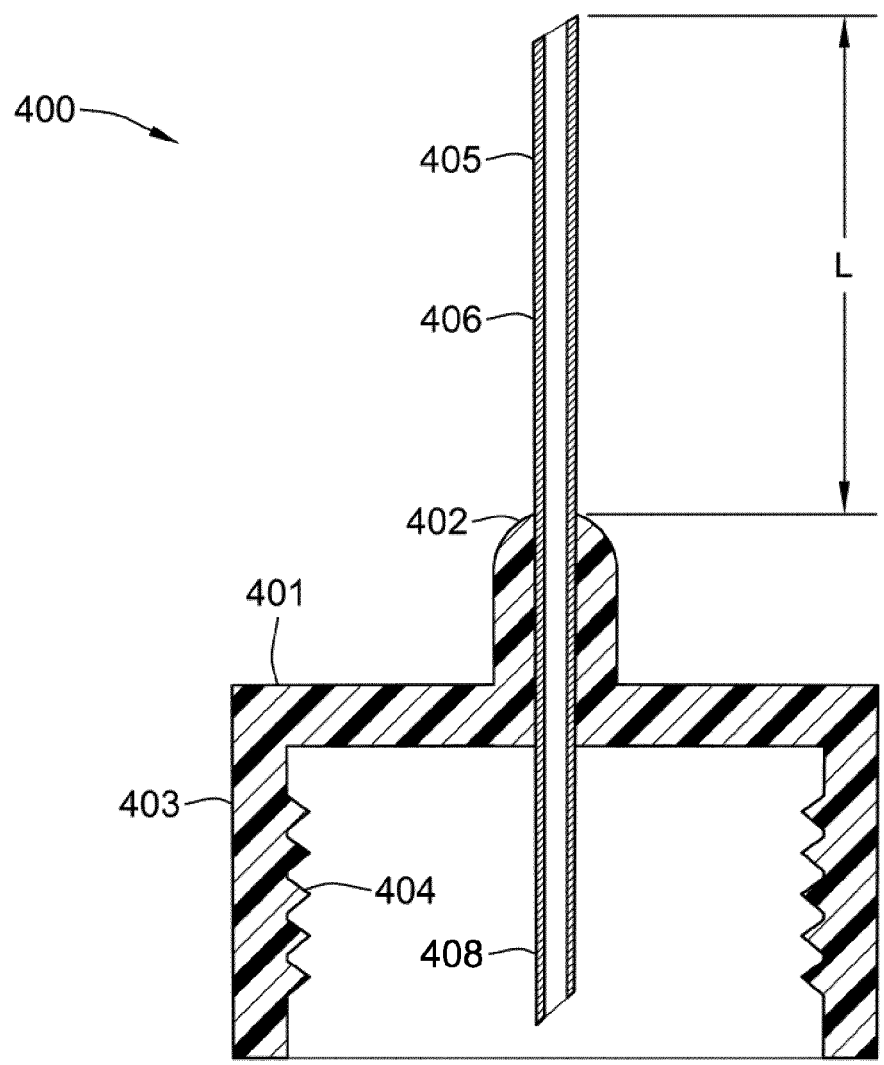
FIG. 6 illustrates one arrangement of a needle assembly that may be mounted on a distal end of the delivery device.
Figure 7:
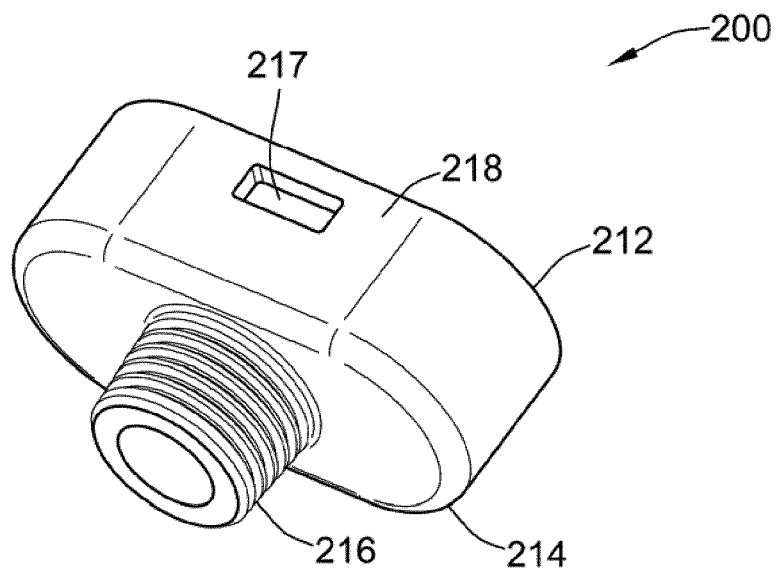
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member of the cartridge housing is provided as the connector 48, which may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
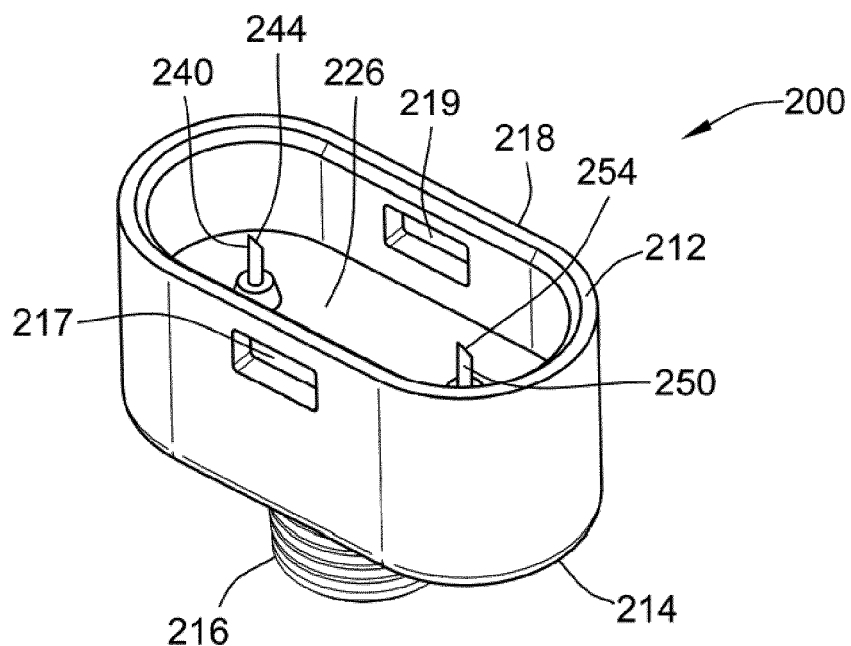
FIG. 8 illustrates another perspective view of the dispense interface illustrated in FIG. 4.
Figure 9:
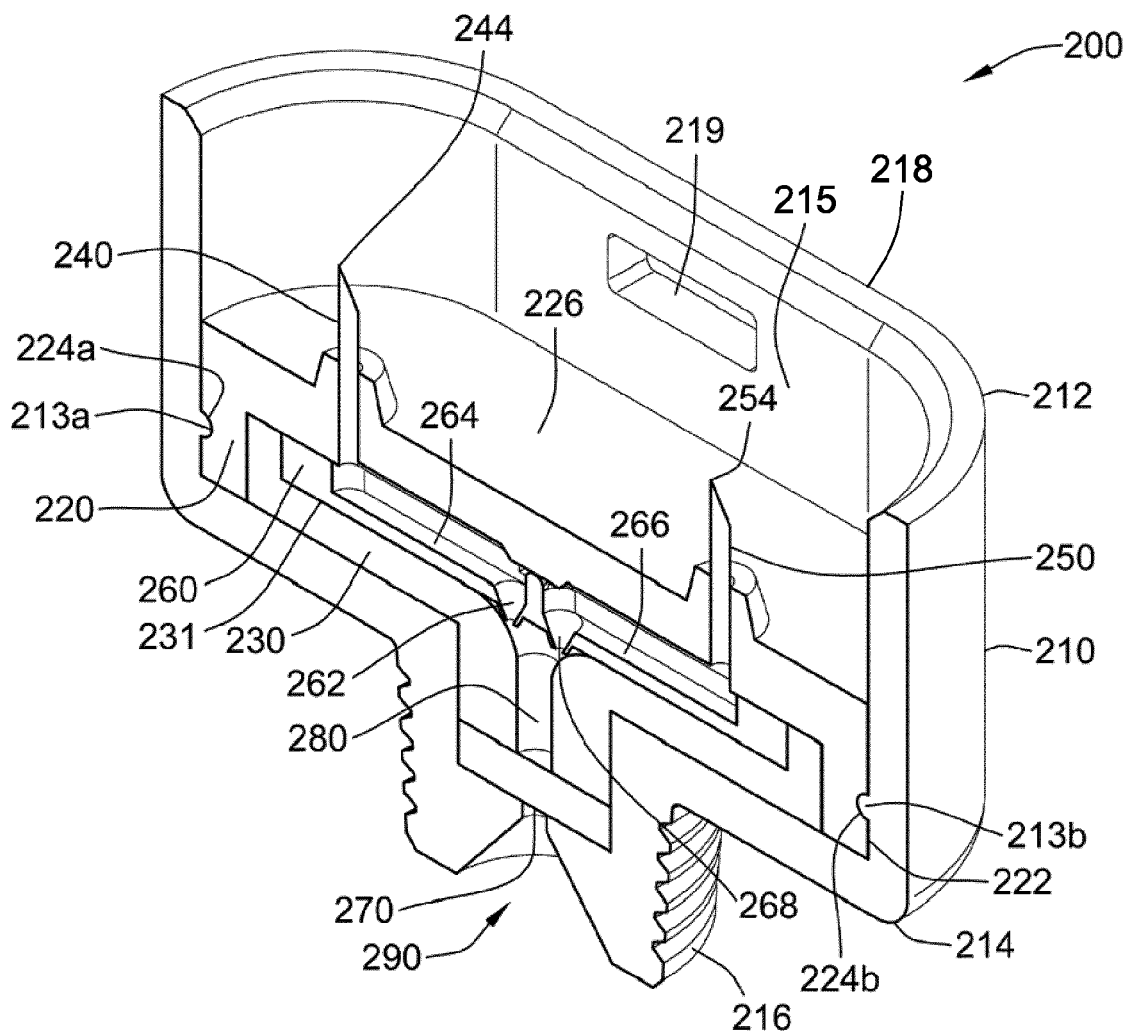
FIG. 9 illustrates a cross-sectional view of the dispense interface illustrated in FIG. 4.
Figure 10:
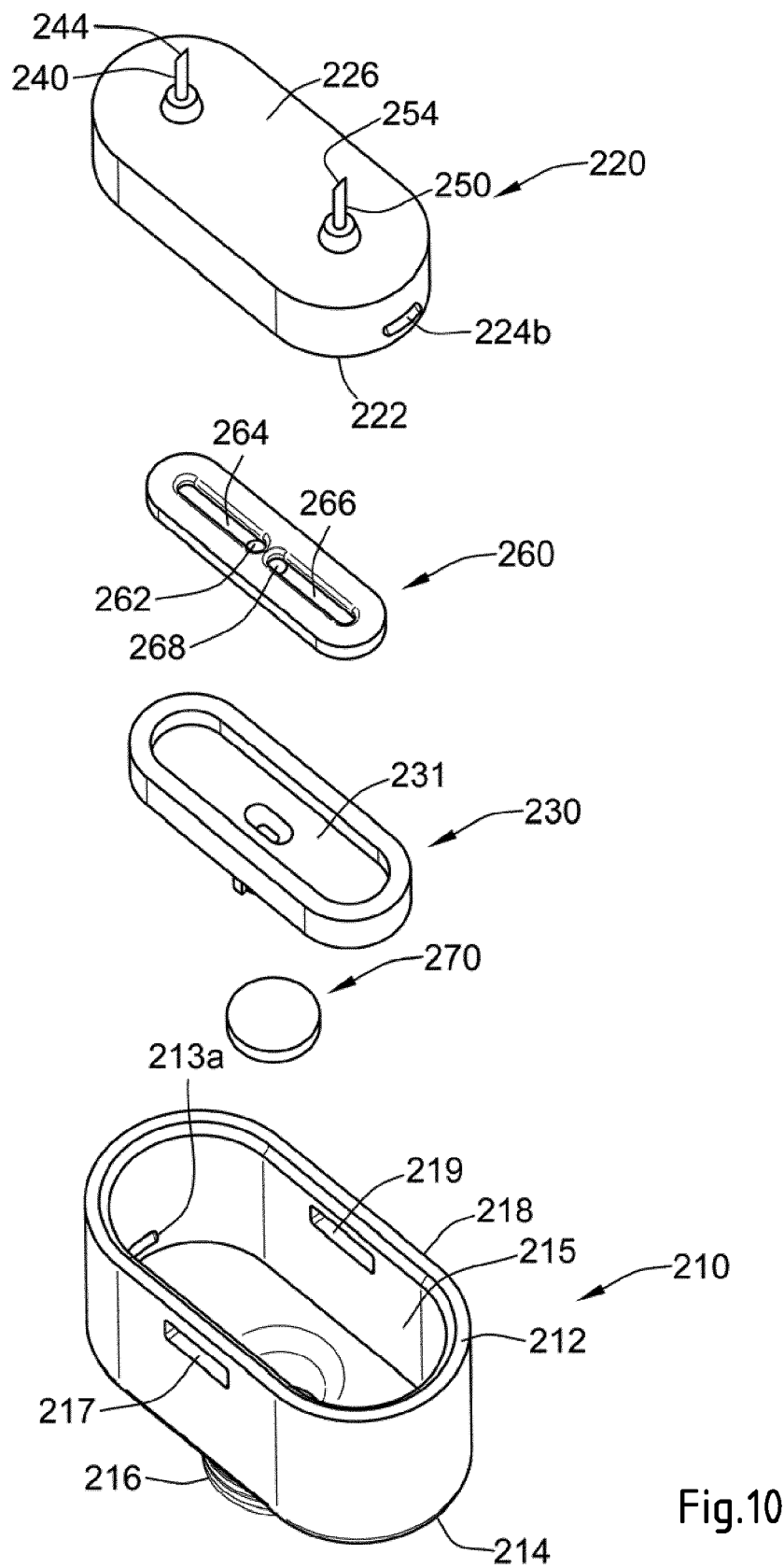
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
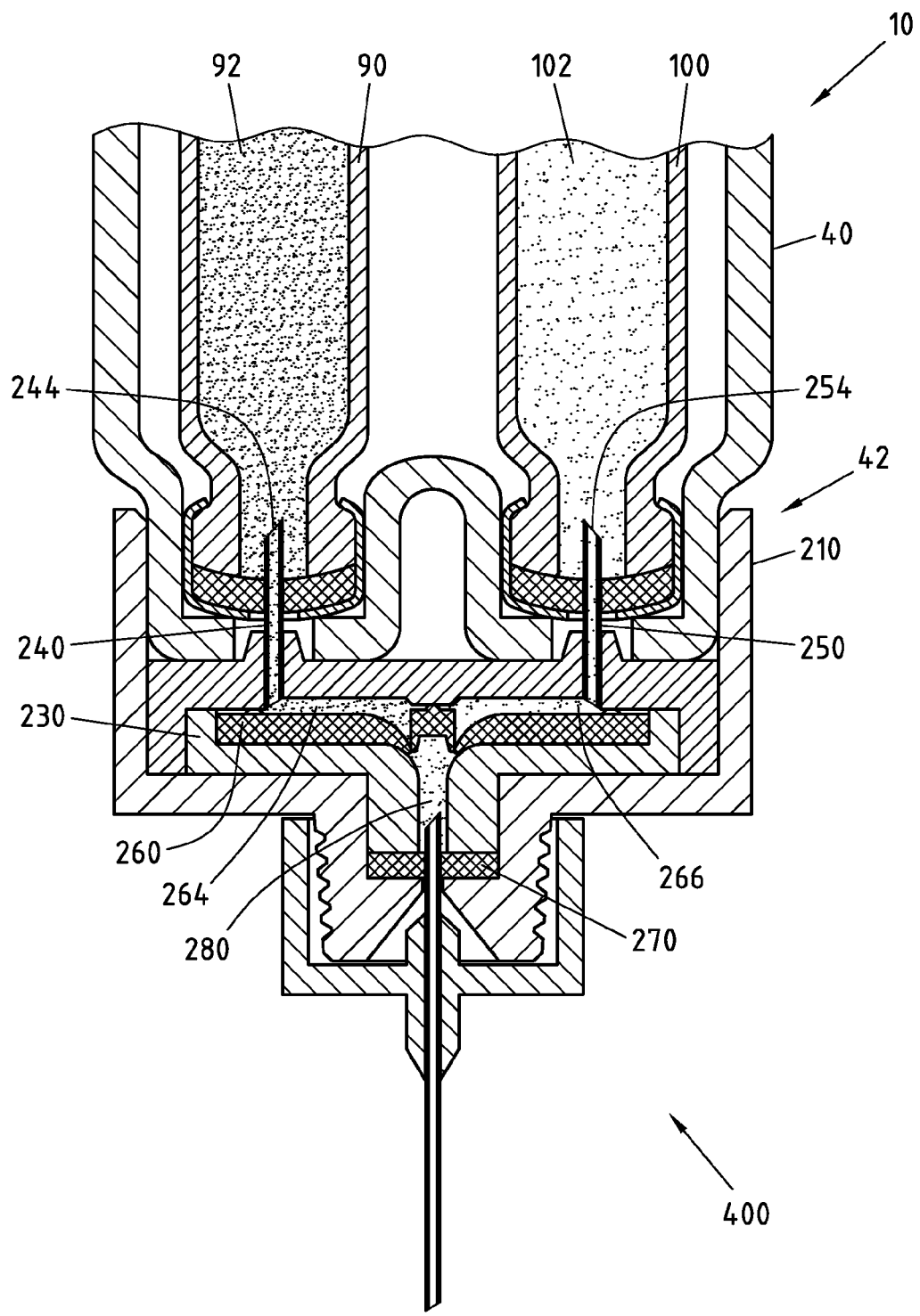
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Dispense interface 200 and needle assembly 400 form a two-part disposable assembly of the delivery device. During normal use, for example, the needle assembly 400 may be intended to be replaced after each injection, whereas the dispense interface 200 may be intended to be replaced after each replacement of at least one of cartridges 90, 100.

The dispense interface 200 and the needle assembly 400 both form part of the ejection channel for ejecting a medicament from at least one of the two cartridges 90, 100 out of distal piercing end 405. As illustrated in FIG. 11, the ejection channel is in particular formed by the lumens of the first and second piercing needles 240, 250, of the first and second fluid grooves 264, 266, of the holding chamber 280 and of the double ended needle 406.

A blocking of the ejection channel may occur in particular within needles 240, 250, 406 because of their small cross section. If a blocking occurs in needle 406 for example, the user may fix the failure by replacing needle assembly 400 by a new one. Likewise, if a blocking occurs in at least one of needles 240, 250, the user may fix the failure by replacing dispense interface 200 by a new one. The channels inside the dispense interface 200 are also narrow so that a blockage can happen here as well. In addition, also the valve system inside the interface can be blocked. Therefore, there are different kinds of causes which may cause a blocking of the ejection channel.

In case of a failure, it is usually not easy or possible for the user to see or to determine, which one of the needles is blocked or whether there is a different cause for the failure. Thus, correction of the failure may not be easy to handle for the user.

Yet, by controlling the delivery device as a function of the actuation step failure number, failure handling may be improved while at the same time maintaining user safety. An example of controlling the delivery device by means of the control unit is now described with reference to FIGS. 12 and 13.

Figure 12:
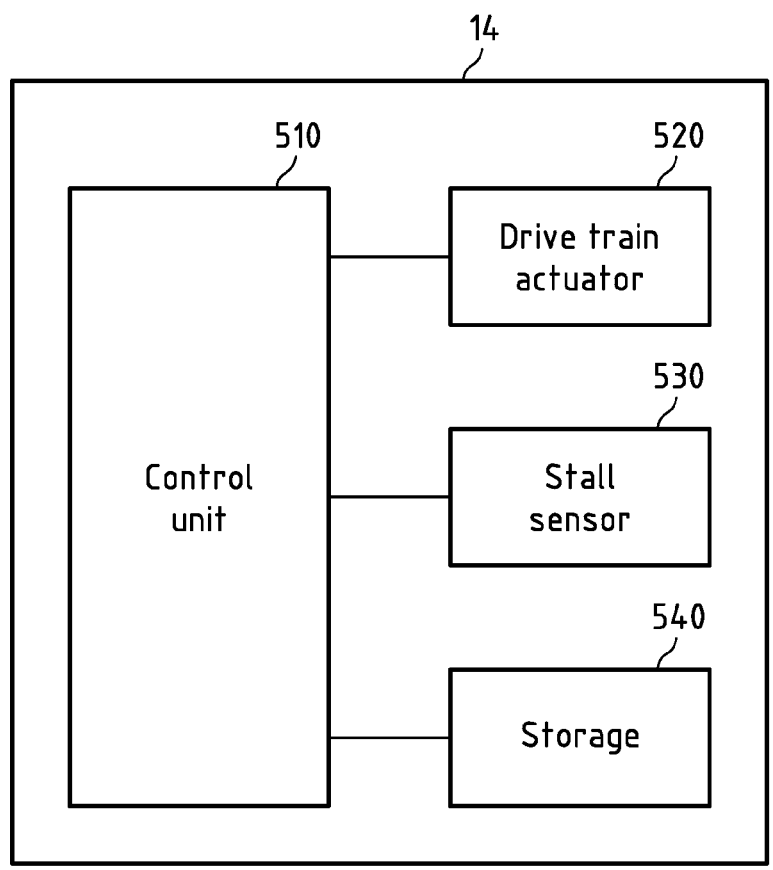
FIG. 12 illustrates a schematic representation of the control unit of the delivery device illustrated in FIG. 1.

FIG. 12 illustrates a schematic representation of the control unit of the delivery device illustrated in FIG. 1. The main body 14 of the delivery device in particular contains the following components:
a. a control unit 510;
b. a drive train actuator 520;
c. a stall sensor 530; and
d. a storage 540.

Control unit 510 may comprise one or more microprocessors and is configured to control the functioning of the delivery device. In particular, control unit 510 is configured to control the drive train actuator 520, which actuates the drive train of the delivery device, i.e. the movement of the drive train for priming or for ejecting a medicament dose from at least one of the two cartridges 90, 100.

Stall sensor 530 is configured to detect stalling of the drive train, for example by monitoring the voltage/current profile of the drive train actuator 520 or by monitoring the signal of an optical sensor that is triggered by one or more flags mounted on the axis of a motor of the drive train, which flags alternately direct light to or block light from the optical sensor. The stall sensor 530 is connected to the control unit 510 so that the control unit 510 may detect a failure of drive train actuation steps by means of the stall sensor 530 detecting stalling of the drive train.

The control unit 510 is further connected to storage 540, which for example may be a RAM, a hard drive, a flash storage or the like. The storage 540 may comprise commands for the control unit 510. These commands comprise a control sequence such as the control sequence illustrated by the flow chart shown in FIG. 13 which is configured to be performed by the control unit 510. Storage 540 may also comprise variables to store the actuation step failure number, replacement number ranges, system failure threshold numbers or the like.

Figure 13:
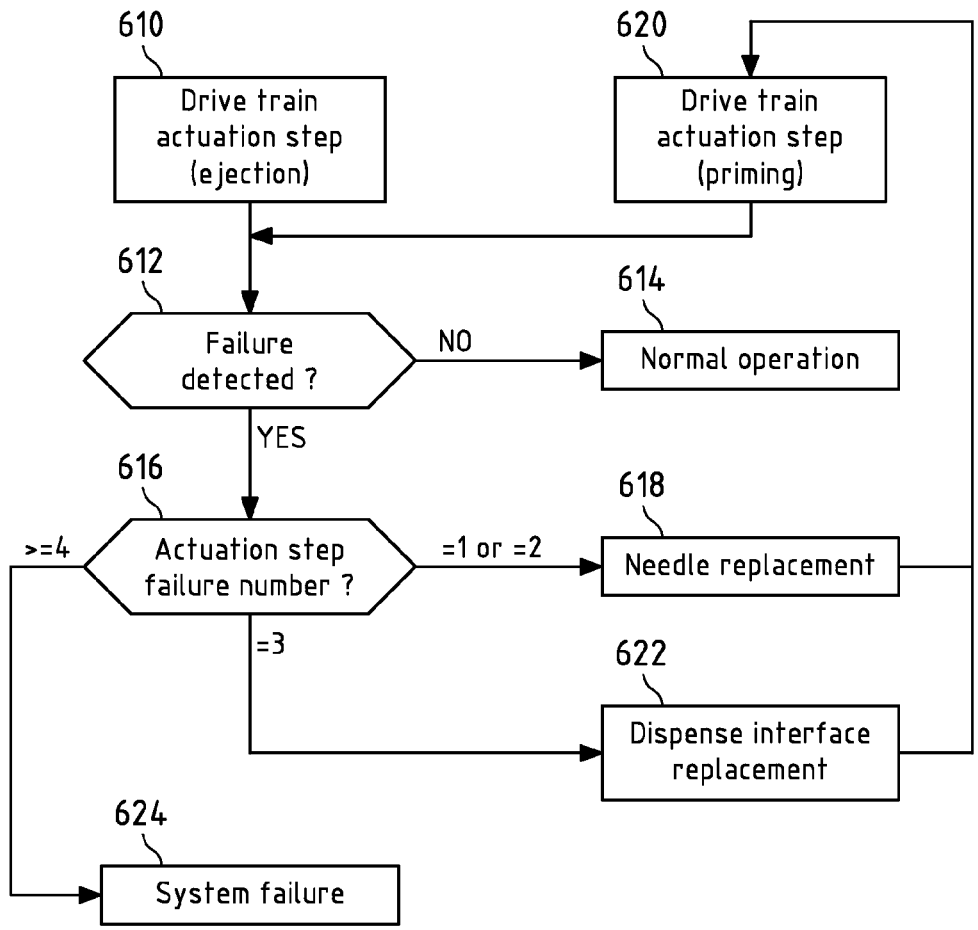
FIG. 13 shows a flow chart of a control sequence for controlling the delivery device as a function of the actuation step failure number.

FIG. 13 shows a flow chart of a control sequence for controlling the delivery device as a function of the actuation step failure number.

It is assumed that at the beginning of the process shown in the flow chart a variable for the actuation step failure number is initiated in storage 540 and set to zero ("0"). If a user presses injection button 74 of the delivery device, control unit 510 may perform a drive train actuation step 610 for medicament dose ejection, in which the control unit 510 controls drive train actuator 520 to move the drive train of the delivery device to exert a pressure on the bung of one or both cartridges 90, 100 in order to eject a respective dose of a medicament.

During drive train actuation, control unit 510 monitors by means of stall sensor 530 whether a stalling of the drive train occurs indicating a failure of the drive train actuation step. If the drive train works properly and no stalling is detected (step 612), control unit 510 continues to control the delivery device according to normal operation (step 614). If however, a failure of the drive train actuation step 610 is detected, control unit 510 increases the actuation step failure number stored in a variable of storage 540 by 1 and proceeds to step 616. In step 616 the delivery device is controlled as a function of the actuation step failure number by comparing the value of the actuation step failure number to different thresholds.

If the actuation step failure number equals 1 or 2, the control unit 510 continues with a needle replacement step 618, in which the control unit 510 requests or forces a replacement of needle assembly 400. In other words, needle assembly 400 in this example corresponds to a first part of a disposable assembly and the according first part replacement number range comprises numbers 1 and 2.

After needle replacement step 618, the process proceeds to drive train actuation step 620. During drive train actuation in step 620, control unit 510 again monitors by means of stall sensor 530 whether a stalling of the drive train occurs indicating a failure of the drive train actuation step. If the drive train works properly and no faulty stalling is detected (step 612), control unit 510 continues to control the delivery device according to normal operation (step 614). For example, the user may then initiate another drive train actuation step for ejection (step 610) by pressing the injection button 74. At the same time, the actuation step failure number is reset in storage 540 to zero ("0").

If, however, another failure is detected in step 612, the control unit 510 increases the actuation step failure number stored in a variable of storage 540 by 1 and proceeds again to step 616.

If at step 616 the actuation step failure number equals 3, the control unit 510 continues with a dispense interface replacement step 622, in which the control unit 510 requests or forces a replacement of dispense interface 200. In other words, dispense interface 200 in this example corresponds to a second part of the disposable assembly and the second part replacement number range only comprises the number 3. After dispense interface replacement step 622, the process proceeds to drive train actuation step 620.

During the needle replacement step 618 or the dispense interface replacement step 622, the control unit 510 may for example cause displaying of a message such as "Error! Please replace needle assembly!" or "Error! Please replace dispense interface!" on digital display 80 in order to request replacement of the needle assembly 400 or the dispense interface 200, respectively. The control unit 510 may also monitor by means of provided sensors, whether the user actually replaces needle assembly 400 or dispense interface 200 in order to ensure that the user does not ignore the error message. Alternatively, if there is no sensor for needle replacement, the apparatus trusts the user that he will replace the needle. In order to increase the likelihood that the user indeed replaces the needle, needle replacement in this example is requested twice before the dispense interface has to be changed.

In the needle or the dispense interface replacement step 618, 622, the control unit 510 also sets the delivery device into a status, in which a further drive train actuation step for fluid dose ejection (step 610), is only allowed after a successful drive train actuation step for priming (step 620). This may be implemented as shown in FIG. 13 in that the control unit 510 directly continues with a drive train actuation step for priming (step 620) after the needle or the dispense interface replacement step 618, 622.

If, finally, the actuation step failure number equals the predetermined system failure threshold number, which in this example equals 4, the control unit 510 continues with system failure step 624, in which the control unit 510 sets the delivery device into a status in which further drive train actuation steps for fluid dose ejection and priming are permanently disallowed. For example the control unit 510 may then also cause displaying of a message such as "Serious error! Please contact service!" on digital display 80.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and >. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. There are also further examples of pharmaceutically acceptable salts.

Pharmaceutically acceptable solvates are for example hydrates.

The invention claimed is:

1. An apparatus for automatic ejection of a dose of medicament, the apparatus comprising:
   a drive train for automatically ejecting a fluid from a fluid reservoir through an ejection channel;
   a housing comprising a connector for removably attaching thereto a disposable assembly that forms a portion of the ejection channel when the disposable assembly is attached to the connector; and
   a control unit configured to:
      detect failures of drive train actuation steps for actuating the drive train for priming or fluid dose ejection,
      control the apparatus as a function of an actuation step failure number that indicates a number of failed drive train actuation steps that have occurred since a last successful drive train actuation step, and
      perform a process comprising:
         detecting a first failure of a drive train actuation step,
         determining that a first actuation step failure number associated with the first failure is within a predetermined first part replacement number range,
         causing a first replacement step to be carried out for replacing a first portion of the disposable assembly based on the predetermined first part replacement number range,
         after causing the first replacement step to be carried out, detecting a second failure of a drive train actuation step,
         determining that a second actuation step failure number associated with the second failure is within a predetermined second part replacement number range, and
         causing a second replacement step to be carried out for replacing a second portion of the disposable assembly based on the predetermined second part replacement number range,
      wherein the predetermined first part replacement number range is different from the predetermined second part replacement number range.

2. The apparatus according to claim 1, wherein the control unit is configured to detect a failure of the drive train actuation step by detecting stalling of the drive train during the drive train actuation step.

3. The apparatus according to claim 1, wherein the disposable assembly is one of a dispense interface with a needle hub to which a disposable needle or a needle assembly can be attached, a needle assembly, or a dispense interface with a needle assembly attached thereto.

4. The apparatus according to claim 1, wherein the apparatus further comprises a display for outputting messages to a user, and the process further comprises outputting of a replacement message to the display.

5. The apparatus according to claim 1, wherein the control unit is further configured to set the apparatus into a status in which a further drive train actuation step for fluid dose ejection is allowed based on detection of a replacement of the first portion or the second portion of the disposable assembly, and wherein the process further comprises setting the apparatus such that the further drive train actuation step is only allowed after a successful drive train actuation step for priming.

6. The apparatus according to claim 1, wherein
the first replacement step comprises outputting a first replacement message to a user at a display of the apparatus,
wherein the second replacement step comprises outputting a second replacement message to the user at the display, and
wherein the process further comprises causing a system failure step to be carried out if the actuation step failure number is equal to or greater than a predetermined system failure threshold number, the system failure step comprising setting the apparatus such that further drive train actuation steps for fluid dose ejection are permanently disallowed.

7. The apparatus according to claim 6, wherein the first replacement step further comprises:
setting the apparatus such that a first further drive train actuation step is only allowed after detection of a replacement of the first portion of the disposable assembly, and
setting the apparatus such that a second further drive train actuation step for fluid dose ejection is only allowed after a successful drive train actuation step for priming.

8. The apparatus according to claim 7, wherein the second replacement step further comprises:
setting the apparatus such that a third further drive train actuation step is only allowed after detection of a replacement of the second portion of the disposable assembly, and
setting the apparatus such that a fourth further drive train actuation step for fluid dose ejection is only allowed after the successful drive train actuation step for priming.

9. The apparatus according to claim 1, wherein the control unit is configured to cause a system failure step when the actuation step failure number is equal to or greater than a predetermined system failure threshold number, the system failure step comprising setting the apparatus such that further drive train actuation steps for fluid dose injection are permanently disallowed.

10. The apparatus according to claim 1, wherein the apparatus comprises a button for initiating a fluid dose ejection step.

11. The apparatus according to claim 1, wherein the apparatus is a medicament injection device.

12. The apparatus according to claim 1, wherein the apparatus is a hand-held apparatus.

13. A system for automatic ejection of a dose of medicament, the system comprising:
a disposable assembly; and
an apparatus to which the disposable assembly is attachable, the apparatus comprising:
a drive train for automatically ejecting a fluid from a fluid reservoir through an ejection channel and through the disposable assembly, the disposable assembly forming a portion of the ejection channel, and
a control unit configured to:
detect failures of drive train actuation steps for actuating the drive train for priming or fluid dose ejection,
control the apparatus as a function of an actuation step failure number that indicates a number of failed drive train actuation steps that have occurred since a last successful drive train actuation step, and
perform a process comprising:
detecting a first failure of a drive train actuation step,
determining that a first actuation step failure number associated with the first failure is within a predetermined first part replacement number range,
causing a first replacement step to be carried out for replacing a first portion of the disposable assembly based on the predetermined first part replacement number range,
after causing the first replacement step to be carried out, detecting a second failure of a drive train actuation step,
determining that a second actuation step failure number associated with the second failure is within a predetermined second part replacement number range, and
causing a second replacement step to be carried out for replacing a second portion of the disposable assembly based on the predetermined second part replacement number range,
wherein the predetermined first part replacement number range is different from the predetermined second part replacement number range.

14. A method of controlling a drive train of an apparatus for automatically ejecting a dose of medicament, the apparatus configured to detect failures of drive train actuation steps for actuating the drive train for priming or for fluid dose ejection and configured to operate as a function of an actuation step failure number that indicates a number of failed drive train actuation steps that have occurred since a last successful drive train actuation step, the method comprising:
detecting a first failure of a drive train actuation step;
determining that a first actuation step failure number associated with the first failure is within a predetermined first part replacement number range;
causing a first replacement step to be carried out for replacing a first portion of the disposable assembly based on the predetermined first part replacement number range;
after causing the first replacement step to be carried out, detecting a second failure of a drive train actuation step;
determining that a second actuation step failure number associated with the second failure is within a predetermined second part replacement number range; and
causing a second replacement step to be carried out for replacing a second portion of the disposable assembly based on the predetermined second part replacement number range wherein the predetermined first part replacement number range is different from the predetermined second part replacement number range.

15. The method according to claim 14, wherein detecting a failure of the drive train actuation step comprises detecting stalling of the drive train.

16. The method according to claim 14, wherein causing the first replacement step or the second replacement step to be carried out comprises outputting a replacement message to a display.

17. The method according to claim 14, wherein causing the first replacement step or the second replacement step to be carried out comprises allowing a further drive train actuation step only after detecting a replacement of the first portion or the second portion of the disposable assembly.

18. The method according to claim 14, wherein causing the first replacement step or the second replacement step to be carried out comprises allowing a further drive train actuation step for fluid dose ejection only after a successful drive train actuation step for priming.

19. The apparatus of claim 1, wherein the control unit is configured to control the apparatus
   such that further drive train actuation steps are prevented when the actuation step failure number exceeds a system failure threshold number.

20. The apparatus of claim 1, wherein the second portion of the disposable assembly comprises a dispense interface configured to be attached to the housing at the connector, and wherein the first portion of the disposable assembly comprises a needle assembly configured to be attached to the dispense interface at a needle hub of the dispense interface.

* * * * *